United States Patent
Lariviere et al.

(10) Patent No.: US 7,223,900 B1
(45) Date of Patent: May 29, 2007

(54) THIN SANITARY NAPKIN ALLOWING FOR CONTROLLED DEFORMATION WHEN IN USE

(75) Inventors: Christiane Lariviere, Montreal (CA); Roya Mohmad, Montreal (CA); Zulfikar Murji, Verdun (CA)

(73) Assignee: Johnson & Johnson Inc., Montreal (CA)

( * ) Notice: Subject to any disclaimer, the term of this patent is extended or adjusted under 35 U.S.C. 154(b) by 0 days.

(21) Appl. No.: 09/374,512

(22) Filed: Aug. 16, 1999

(51) Int. Cl.
*A61F 13/15* (2006.01)
*A61F 13/20* (2006.01)

(52) U.S. Cl. .................. 604/380; 604/385.01; 604/378
(58) Field of Classification Search .............. 604/358, 604/367, 378, 381, 383, 385.01, 385.03, 604/385.05, 374, 385.23, 385.31, 369, 385.04, 604/380

See application file for complete search history.

(56) References Cited

U.S. PATENT DOCUMENTS

| | | | | |
|---|---|---|---|---|
| 4,337,772 A | * | 7/1982 | Roeder | 604/387 |
| 4,518,451 A | * | 5/1985 | Luceri et al. | 156/202 |
| 5,069,676 A | * | 12/1991 | Ito et al. | 604/358 |
| 5,171,302 A | * | 12/1992 | Buell | 604/385.1 |
| 5,197,959 A | * | 3/1993 | Buell | 604/385.1 |
| 5,374,260 A | | 12/1994 | Lemay et al. | 604/378 |
| 5,466,232 A | | 11/1995 | Cadieux et al. | 604/378 |
| 5,505,719 A | * | 4/1996 | Cohen et al. | 604/372 |
| 5,575,786 A | | 11/1996 | Osborn, III | |
| 5,578,025 A | * | 11/1996 | May | 604/385.1 |
| 5,891,121 A | * | 4/1999 | Redwine et al. | 604/387 |
| 6,007,528 A | * | 12/1999 | Osborn, III | 604/387 |
| 6,093,871 A | * | 7/2000 | Takai et al. | 604/383 |
| 6,413,248 B1 | * | 7/2002 | Mizutani | 604/385.17 |

FOREIGN PATENT DOCUMENTS

| | | |
|---|---|---|
| DE | 297 03 589 U1 * | 7/1997 |
| EP | 0 293 208 A1 * | 11/1988 |
| EP | 0 705 585 A1 | 4/1996 |
| EP | 0 852 938 A2 * | 7/1998 |
| WO | WO 95/07674 | 3/1995 |
| WO | WO 95/07674 A2 | 3/1995 |

* cited by examiner

Primary Examiner—Michele Kidwell

(57) ABSTRACT

The present invention provides a sanitary napkin that is thin (less than 5 mm in thickness), highly absorbent and has a lateral flexibility allowing for controlled deformation when in use, namely the assumption of a "W" pattern. This controlled deformation provides a good comfort potential and simultaneously reduces the likelihood of bunching due to compression forces exerted laterally against the napkin by the thighs of the wearer. In a specific example, the sanitary napkin is characterized by a pair of preferential bending zones extending along the longitudinal axis of the sanitary napkin and by a pair of longitudinal adhesive zones on the liquid-impervious barrier layer of the sanitary napkin, that register with the preferential bending zones. The longitudinal adhesive zones fasten the sanitary napkin to the undergarment at the areas at which the sanitary napkin is intended to fold when subjected to lateral compression. This feature allows the napkin to fold and adopt a desired three-dimensional deformation profile in a predictable manner when laterally compressed.

13 Claims, 3 Drawing Sheets

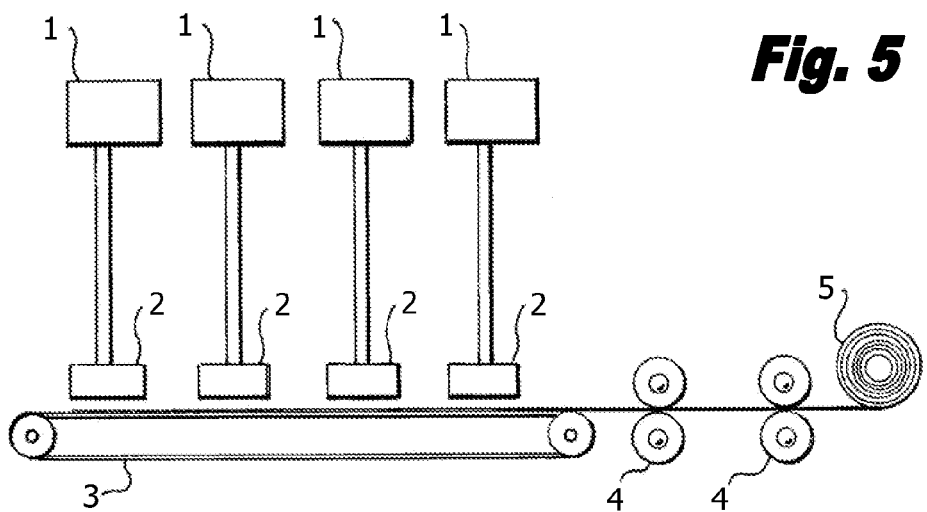
Fig. 5
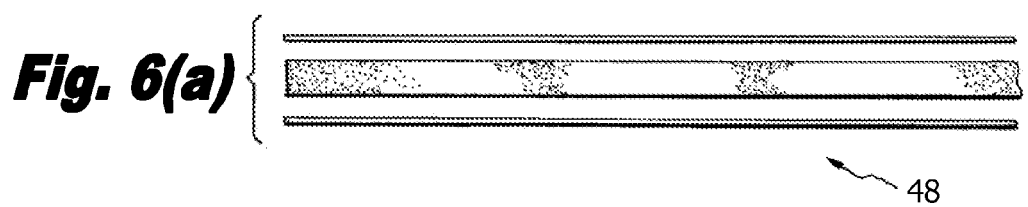
Fig. 6(a)
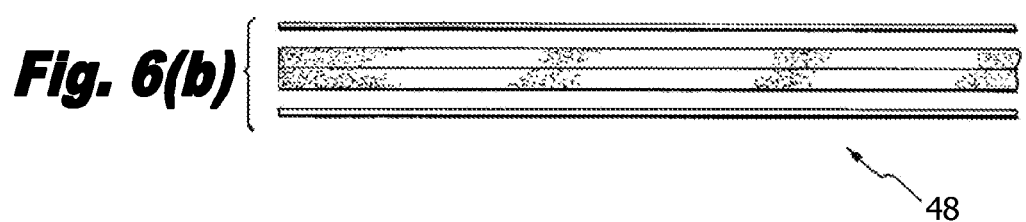
Fig. 6(b)
Fig. 7
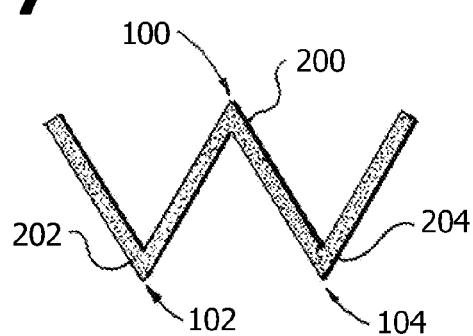

THIN SANITARY NAPKIN ALLOWING FOR CONTROLLED DEFORMATION WHEN IN USE

FIELD OF THE INVENTION

The present invention relates generally to the art of fluid absorption and more particularly to a disposable sanitary napkin is thin, highly absorbent and is capable of controlled deformation when in use.

BACKGROUND OF THE INVENTION

One element that contributes to the performance of a sanitary napkin is the way the napkin withstands deformation when in use. It has been observed that the thighs of an individual exert lateral forces on a sanitary napkin when the article is positioned for use on the undergarment. This results in bunching of the sanitary napkin, affecting the efficiency of the article's ability to collect bodily fluids since there is a reduction in the article's surface area. This observation is especially true for thin sanitary napkins that are highly flexible.

One approach to minimising this problem is to make the sanitary napkin stiffer in order that it may better withstand the effects of lateral compression. This approach may, however, have an adverse effect on the comfort potential of the sanitary napkin because the added stiffness affects the movement of the napkin in all directions, making it more difficult for the napkin to conform to the natural shape of the wearer's body.

Against this background, it can be seen that there exists a need to provide a sanitary napkin that is comfortable and yet reduces the likelihood of bunching when in use, leading to an overall increase in its efficiency for collecting bodily fluids.

SUMMARY OF THE INVENTION

In one aspect, the sanitary napkin according to the invention is provided with at least a pair of preferential bending zones in its absorbent system, laterally (transversely) spaced apart from one another, that extend along the longitudinal axis of the sanitary napkin. The sanitary napkin also includes lateral positioning adhesive zones that also extend along the longitudinal axis of the sanitary napkin and register with the respective preferential bending zones. The lateral positioning adhesive zones contribute to fasten the sanitary napkin to the undergarment of the wearer at areas that generally coincide with the preferential bending zones. The effect of this construction is to promote the folding of the absorbent system at the preferential bending zones and to promote the formation of a certain three-dimensional deformation profile in the sanitary napkin in response to lateral compression exerted by the thighs of the wearer.

In a specific example of implementation of the invention, the absorbent system of the sanitary napkin further includes a central preferential bending zone extending longitudinally in the central portion of the absorbent system, between the preferential bending zones. In use, the sanitary napkin under this specific example of implementation assumes a three-dimensional deformation profile in response to the lateral forces exerted by the thighs of the wearer, which resembles the letter "W".

It has been found beneficial, although not essential to provide the sanitary napkin with a flexural resistance that is not less than about 400 g. This feature provides a sanitary napkin that is sufficiently stiff, so as to be stable enough and thus allow the sanitary napkin to fold in a predictable manner and avoid the likelihood of bunching when subjected to lateral compression.

Other aspects and features of the present invention will become apparent to those ordinarily skilled in the art upon review of the following description of specific embodiments of the invention in conjunction with the accompanying drawings.

DESCRIPTION OF THE DRAWINGS

FIG. 5 is a schematic illustration of means for air-laying absorbent material for making an example of an absorbent layer of the absorbent system of the sanitary napkin according to the invention, using four air-laying heads followed by means for compacting the air-laid material; and FIGS. 6(a) and 6(b) show three and four stratum embodiments, respectively, of an absorbent layer that can be used in the construction of the absorbent system of the sanitary napkin in accordance with the invention;

FIG. 7 is a cross-sectional view of the sanitary napkin shown in FIG. 1, depicting the napkin folded according to a "W" pattern.

DETAILED DESCRIPTION

Figure 1:
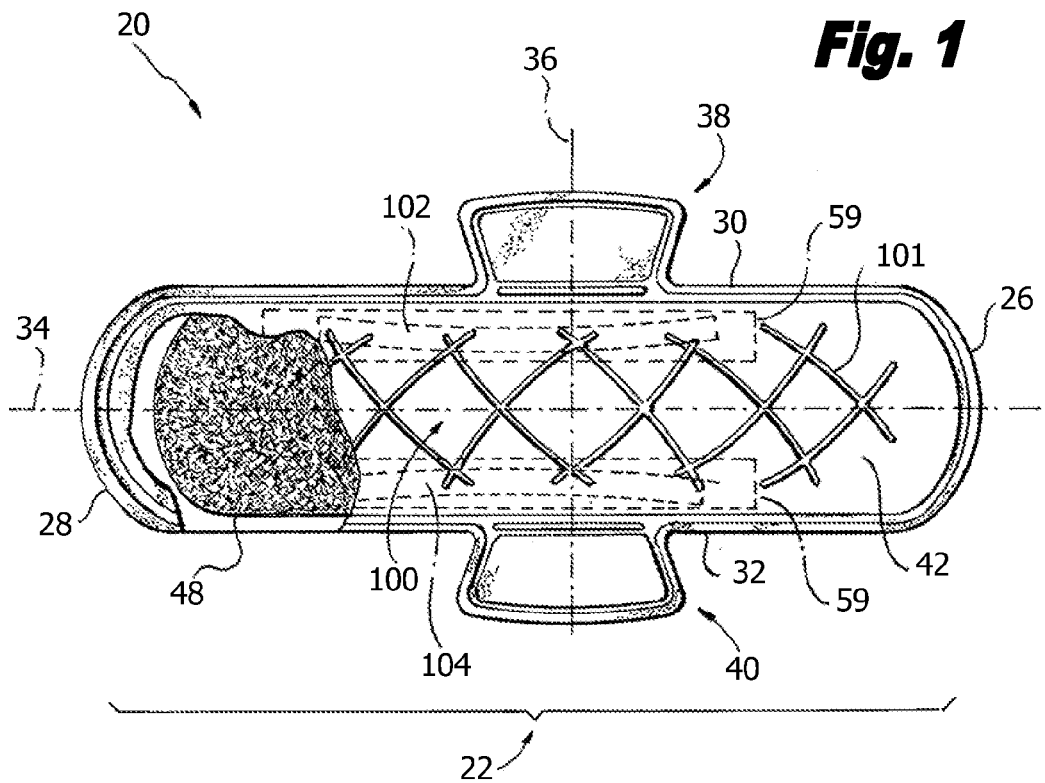
FIG. 1 is a top elevational view of a sanitary napkin in accordance with the present invention, the cover layer of the sanitary napkin being partly removed to show the absorbent system.
Figure 2:
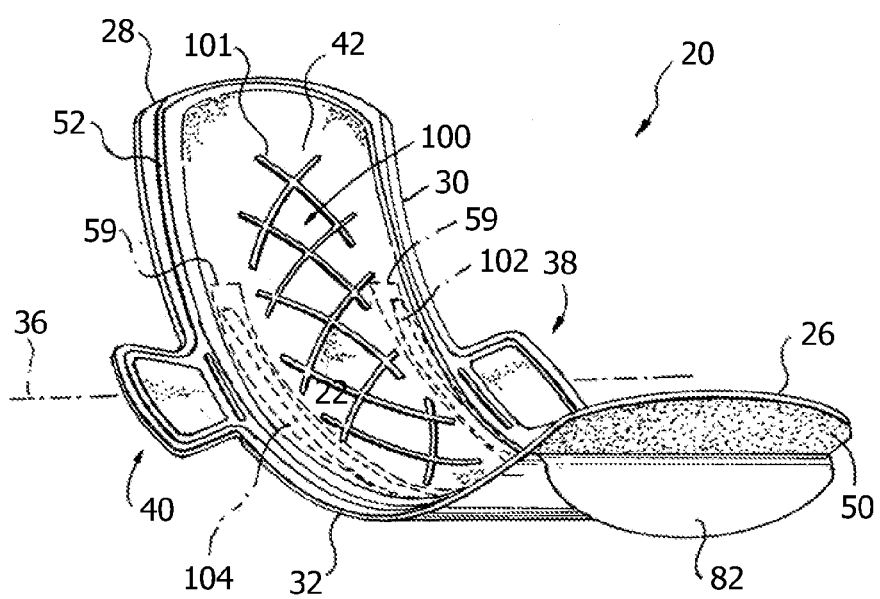
FIG. 2 is a perspective view of the sanitary napkin of FIG. 1, depicted in a position attained when the sanitary napkin is placed in the undergarment of a wearer. This position is a position where no lateral compression is applied on the sanitary napkin.

Referring to FIGS. 1 and 2, there is shown an embodiment of the present invention, a feminine sanitary napkin 20.

The sanitary napkin 20 has a main body 22 with a first transverse side 26 defining a front portion thereof and a second transverse side 28 defining a rear portion thereof. Each of these sides is arcuate or of any other suitable shape. The main body also has two longitudinal sides, namely a first longitudinal side 30 and an opposite second longitudinal side 32. The sanitary napkin 20 has a thickness not exceeding about 5 mm. Preferably, the thickness is less than 3.5 mm, more preferably less than 3 mm, and most preferably, it is of about 2.8 mm.

The sanitary napkin 20 has a longitudinal centerline 34 that is an imaginary line bisecting the sanitary napkin 20 in two identical halves.

The sanitary napkin 20 shown in the drawings has flaps 38, 40. The flaps 38, 40 project laterally outward from each of the longitudinal sides 30, 32. The flaps 38, 40 are in the shape of an isosceles trapezoid with the top adjoining the longitudinal side and the base at the distal end. This is an example only as other flap shapes can also be used without departing from the spirit of the invention. Furthermore, the present invention is not limited to a sanitary napkin with flaps as the present inventive concept can also be embodied in a sanitary napkin without flaps.

The main body 22 also has an imaginary transverse centerline 36 perpendicular to the longitudinal centerline 34 and simultaneously bisecting the flaps 38, 40.

Figure 4:
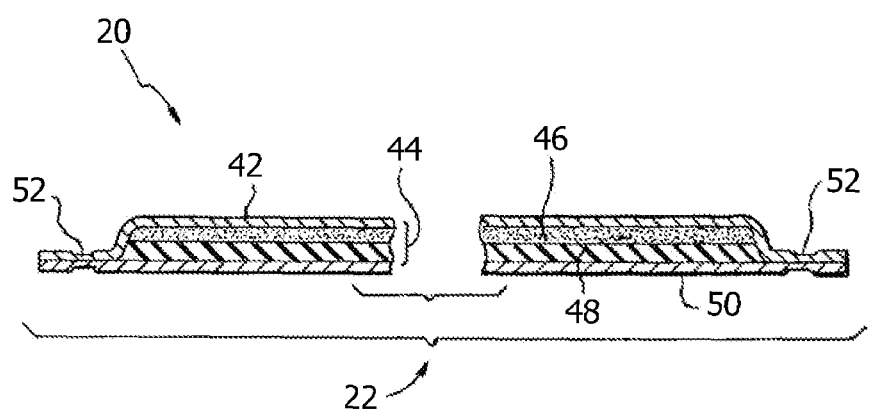
FIG. 4 is a cross-sectional view taken along the longitudinal centerline of the sanitary napkin shown in FIG. 3.

As depicted in FIG. 4, the main body 22 is of a laminate construction and preferably comprises a fluid-permeable cover layer 42, an absorbent system 44, and a fluid-impervious barrier layer 50. The absorbent system has preferably two components, namely a first absorbent layer 46 (commonly known as "transfer layer") and a second absorbent layer 48 (commonly known as "absorbent core"). Alternatively, a single layer, namely the second absorbent layer 48, can form the absorbent system 44. Each of these layers is described in hereinbelow.

Main Body—Cover Layer

The cover layer 42 may be a relatively low density, bulky, high-loft non-woven web material. The cover layer 42 may be composed of only one type of fiber, such as polyester or polypropylene or it may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof. An example is the non-woven cover layer of sanitary napkins sold by Johnson & Johnson Inc. of Montreal, Canada under the trademark Stayfree Ultra-Thin Cottony Dry Cover.

Bi-component fibers may be made up of a polyester core and a polyethylene sheath. The use of appropriate bi-component materials results in a fusible non-woven fabric. Examples of such fusible fabrics are described in U.S. Pat. No. 4,555,446 issued Nov. 50, 1985 to Mays. Using a fusible fabric increases the ease with which the cover layer may be mounted to the adjacent first absorbent layer and/or to the barrier layer.

The cover layer 42 preferably has a relatively high degree of wettability, although the individual fibers comprising the cover may not be particularly hydrophilic. The cover material should also contain a great number of relatively large pores. This is because the cover layer 42 is intended to take-up body fluid rapidly and transport it away from the body and the point of deposition. Advantageously, the fibers which make up the cover layer 42 should not lose their physical properties when they are wetted, in other words they should not collapse or lose their resiliency when subjected to water or body fluid. The cover layer 42 may be treated to allow fluid to pass through it readily. The cover layer 42 also functions to transfer the fluid quickly to the other layers of the absorbent system 44. Thus, the cover layer 42 is advantageously wettable, hydrophilic and porous. When composed of synthetic hydrophobic fibers such as polypropylene or bi-component fibers, the cover layer 42 may be treated with a surfactant to impart the desired degree of wettability.

Alternatively, the cover layer 42 can also be made of polymer film having large pores. Because of such high porosity, the film accomplishes the function of quickly transferring body fluid to the inner layers of the absorbent system. Apertured co-extruded films such as described in U.S. Pat. No. 4,690,679 and available on sanitary napkins sold by Johnson & Johnson Inc. of Montreal, Canada could be useful as cover layers in the present invention.

The cover layer 42 may be embossed to the remainder of the absorbent system 44 in order to aid in promoting fluid transport by fusing the cover to the next layer. Such fusion may be effected locally, at a plurality of sites or over the entire contact surface of cover layer 42 with absorbent system 44. Alternatively, the cover layer 42 may be attached to the absorbent system 44 by other means such as by adhesive.

Main Body—Absorbent System—First Absorbent Layer

Adjacent to the cover layer 42 on its inner side and bonded to the cover layer 42 is a first absorbent layer 46 that forms part of the absorbent system 44. The first absorbent layer 46 provides the means of receiving body fluid from the cover layer 42 and holding it until an underlying second absorbent layer has an opportunity to absorb the fluid.

The first absorbent layer 46 is, preferably, more dense than and has a larger proportion of smaller pores than the cover layer 42. These attributes allow the first absorbent layer 46 to contain body fluid and hold it away from the outer side of the cover layer 42, thereby preventing the fluid from re-wetting the cover layer 42 and its surface. However, the first absorbent layer 46 is, preferably, not so dense as to prevent the passage of the fluid through the layer 46 into the underlying second absorbent layer 48. These types of absorbent layers are commonly known as fluid transfer layers or acquisition layers.

The first absorbent layer 46 may be composed of fibrous materials, such as wood pulp, polyester, rayon, flexible foam, or the like, or combinations thereof. The first absorbent layer 46 may also comprise thermoplastic fibers for the purpose of stabilizing the layer and maintaining its structural integrity. The first absorbent layer 46 may be treated with surfactant on one or both sides in order to increase its wettability, although generally the first absorbent layer 46 is relatively hydrophilic and may not require treatment. The first absorbent layer 46 is preferably bonded on both sides to the adjacent layers, i.e. the cover layer 42 and an underlying second absorbent layer 48. An example of a suitable first absorbent layer is a through air bonded pulp sold by BUCKEYE of Memphis Tenn. under the designation VIZORB 3008.

Main Body—Absorbent System—Second Absorbent Layer

Immediately adjacent to and bonded to the first absorbent layer 46 is the second absorbent layer 48.

In one embodiment, the first absorbent layer 46 has a central width that is at least about the same as the central width of the second absorbent layer 48. In a specific embodiment, this central width is greater than about 64 mm. In another embodiment, the first absorbent layer 46 has a central width that exceeds the central width of the second absorbent layer 48. The term "central width" refers to a specific area of a layer, such as an absorbent layer determinable as follows. A reference point on the sample layer that is disposed beneath the center of the vaginal orifice, when worn is located. A plane parallel to the transverse centerline 36 and 3.75 centimeters forward from the reference point in the direction of the wearers mons pubis is located. Another plane parallel to the lateral centerline 36 and 5.0 centimeters rearward from the reference point in the direction of the wearers buttocks is also located. The greatest flat-out, uncompressed, unmanipulated, lateral width of the sample layer between the two planes is the absorbent width of the sample layer.

The central width of the absorbent system, when the absorbent system includes a plurality of absorbent layers is the central width of the layer of the absorbent system that has the largest central width. In a specific example, the central width of the absorbent system exceeds 64 mm.

In one embodiment, the second absorbent layer 48 is a blend or mixture of cellulosic fibers and superabsorbent disposed in and amongst fibers of that pulp.

In a specific example, the second absorbent layer 48 is a material containing from about 40 weight percent to about 95 weight percent cellulosic fibers; and from about 5 weight percent to about 60 weight percent SAP (superabsorbent polymers). The material has a water content of less than about 10 weight percent. As used herein, the phrase "weight percent" means weight of substance per weight of final material. By way of example, 10 weight percent SAP means 10 g/m2 SAP per 100 g/m2 basis weight of the material.

Cellulosic fibers that can be used in the second absorbent layer 48 are well known in the art and include wood pulp, cotton, flax and peat moss. Wood pulp is preferred. Pulps can be obtained from mechanical or chemi-mechanical, sulfite, kraft, pulping reject materials, organic solvent pulps, etc. Both softwood and hardwood species are useful. Softwood pulps are preferred. It is not necessary to treat cellulosic fibers with chemical debonding agents, cross-linking agents and the like for use in the present material.

The second absorbent layer 48 can contain any superabsorbent polymer (SAP), which SAPs are well known in the art. For the purposes of the present invention, the term "superabsorbent polymer" (or "SAP") refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. Preferred superabsorbent polymer particles for use in the present invention are crosslinked polyacrylates, such as the product offered by Sumitomo Seika Chemicals Co., Ltd. Of Osaka, Japan, under the designation of SA60N Type II*, and the product offered by Chemdal International, Inc. of Palatine, Ill., under the designation of 2100A*.

In a specific example the second absorbent layer 48 is a material containing from about 50 to about 95 weight percent cellulosic fibers and, more specifically from about 60 to about 80 weight percent cellulosic fibers. Such a material may contain from about 5 to about 60 weight percent SAP, preferably from about 20 to about 55 weight percent SAP, even more preferably from about 30 to about 45 weight percent SAP, and most preferably about 40 weight percent SAP.

The second absorbent layer 48 can be manufactured by using air-laying means well known in the art (See FIG. 5). In accordance with FIG. 5, cellulosic fibers (e.g., pulp) are processed using a hammer mill to individualize the fibers. The individualized fibers are blended with SAP granules in a blending system 1 and pneumatically conveyed into a series of forming heads 2. The blending and distribution of fibers and SAP granules can be controlled separately for each forming head. Controlled air circulation and winged agitators in each chamber produce uniform mixture and distribution of pulp and SAP. The SAP can be thoroughly and homogeneously blended throughout the material or contained only in specific strata by distributing it to selected forming heads. Fibers (and SAP) from each forming chamber are deposited by vacuum onto a forming wire 3 thus forming a layered absorbent web. The web is subsequently compressed using calenders 4 to achieve desirable density. The densified web is wound into a roll 5 using conventional winding equipment. The forming wire 3 can be covered with tissue paper to reduce the loss of material. The tissue paper layer can be removed prior to calendering or incorporated into the formed material. In a possible variant, the first absorbent layer 46 can be formed integrally with the second absorbent layer 48 to provide a unitized absorbent system 44. This can be achieved by providing the apparatus depicted in FIG. 5 with an additional forming head (not shown in the drawings) to deposit on the second absorbent layer 48, by air laying and prior to calendering, a layer of material to form the first absorbent layer 46.

The second absorbent layer 48 of the present invention is of high density and in a specific example has a density of greater than about 0.25 g/cc. Specifically, the second absorbent layer 48 may have a density in the range of from about 0.30 g/cc to about 0.50 g/cc. More specifically, the density is from about 0.30 g/cc to about 0.45 g/cc and, even more specifically from about 0.35 g/cc to about 0.40 g/cc.

Air-laid absorbents are typically produced with a low density. To achieve higher density levels, such as the examples of the second absorbent layer 48 given above, the air-laid material is compacted using calenders as shown in FIG. 5. Compaction is accomplished using means well known in the art. Typically such compaction is carried out at a temperature of about 100 degrees C. and a load of about 130 Newtons per millimeter. The upper compaction roll is typically made of steel while the lower compaction roll is a flexroll having a hardness of about 85 SH D. It is preferred that both the upper and lower compaction rolls be smooth, although the upper roll can be engraved.

In one embodiment the second absorbent layer 48 has a ratio of Gurley stiffness, measured in milligrams (mg) to density, measured in grams per cubic centimeter (g/cc), of less than about 3700. In a specific example, that ratio of Gurley stiffness to density is less than about 3200 and, more specifically, less than about 3000.

Gurley stiffness is one of many indices of softness. Gurley stiffness measures the bendability or flexibility of absorbent materials. The lower the Gurley stiffness value, the more flexible the material. The Gurley stiffness values are measured using a Gurley Stiffness Tester (Model No. 4171 E), manufactured by Gurley Precision Instruments of Troy, N.Y. The instrument measures the externally applied moment required to produce a given deflection of a test strip of specific dimensions fixed at one end and having a concentrated load applied to the other end. The results are obtained in "Gurley Stiffness" values in units of milligrams.

The second absorbent layer 48 is strong in light of its softness. Pad integrity is a well-known measurement of absorbent material strength. In a specific embodiment the second absorbent layer 48 demonstrates strength (high pad integrity) over a wide range of densities. In a specific example the second absorbent layer 48 has a pad integrity, measured in Newtons (N), to density (g/cc) ratio of greater than about 25.0. In a more specific example, that ratio is greater than about 30.0 and, could even be greater than about 35.0. The pad integrity is a test performed on an Instron Universal Testing Machine. Essentially, the test measures the load required to pierce through the test sample, as described in the PFI Method of 1981. A test sample having dimensions of 50 mm by 50 mm is clamped on the Instron with a suitable fastening device. A 20 mm diameter piston traveling at the rate of 50 mm/min punctures the stationary sample. The force required to puncture the sample is measured in Newtons (N).

The second absorbent layer 48 can be prepared over a wide range of basis weights. The second absorbent layer 48 can have a basis weight in the range of from about 100 g/m2 to about 700 g/m2. In a specific example, the basis weight ranges from about 150 g/m2 to about 350 g/m2. Preferably the basis weight ranges from about 200 g/m2 to about 300 g/m2 and, more preferably, to about 250 g/m2.

The second absorbent layer 48 can be formed as three or four lamina or strata. Those strata include a bottom layer, one or two middle layers and a top layer. Specific examples of three and four layer material are set forth below. The SAP can be included in any or all of the layers. The concentration (weight percent) of SAP in each layer can vary as can the nature of the particular SAP.

An interesting characteristic of the second absorbent layer 48 is its ability to retain SAP when subjected to mechanical stress. The second absorbent layer 48 retained over 85 percent by weight of its SAP content when subjected to 10 minutes of rigorous shaking. Specifically, a material of this invention retains over 90 percent, more specifically over 95 percent and, even more specifically over 99 percent of its SAP under these mechanical stresses. The percent of SAP retained was determined by shaking the material in a Ro-Tap Sieve Shaker manufactured by W. S. Tyler Co., Cleveland Ohio. More specifically the sample is placed in a 28-mesh (Tyler series) sieve. Additional sieves of 35-mesh and 150-mesh were attached to the first sieve forming a column of increasingly fine sieves. The column of sieves was capped on either end to prevent the loss of fiber and/or SAP. The sieve column was placed in the shaker and agitated for 10 minutes. The amount of SAP granules shaken loose from the sample, "free SAP", was determined by combining the residue contained in each of the sieves and separating the cellulosic fiber from the SAP.

Even where prepared as from multiple layers, the final thickness of the formed second absorbent layer 48 is low. The thickness can vary from about 0.5 mm to about 2.5 mm. In a specific example, the thickness is from about 1.0 mm to about 2.0 mm and, even more specifically from about 1.25 mm to about 1.75 mm.

One embodiment of the second absorbent layer 48 particularly well suited for use in the sanitary napkin 20 is depicted in FIG. 6. Such second absorbent layer 48 has a basis weight of from about 200 g/m2 to about 350 g/m2 and a density between about 0.3 g/cc and 0.5 g/cc. In a specific example, the density is from about 0.3 g/cc to about 0.45 g/cc and, more specifically about 0.4 g/cc.

The second absorbent layer 48 depicted in FIG. 6(a) is air-laid as three strata: a bottom layer of pulp (without superabsorbent) with a basis weight of about 25 g/m2; a middle layer with a basis weight of about 150 g/m2 and which contains from about 10 to about 30 g/m2 superabsorbent and from about 120 g/m2 to about 140 g m2 pulp; and a top layer of pulp (without superabsorbent) with a basis weight of about 25 g/m2. Relative to the total basis weight of the second absorbent layer 48, the level of superabsorbent ranges from about 5 to about 15 weight percent (g/m2 of superabsorbent per g/m2 material). In a specific example, the level of superabsorbent is from about 7.5 weight percent to about 12.5 weight percent of the material. More specifically, the material contains about 10 weight percent of superabsorbent. Thus, the middle layer of the material could contain from about 15 g/m2 to about 25 g/m2 superabsorbent and from about 125 g/m2 to about 135 g/m2 pulp and, more specifically about 20 g/m2 superabsorbent and about 130 g/m2 pulp. The middle layer containing pulp and superabsorbent can be laid down as a homogeneous blend or as a heterogeneous blend wherein the level of superabsorbent varies with proximity to the bottom layer.

In another embodiment depicted in FIG. 6(b), the second absorbent layer 48 is air-laid as four strata. In this embodiment, the middle layer referred to above is replaced with two middle layers: a first middle layer adjacent the top layer and a second middle layer adjacent the bottom layer. Each of the first and second middle layers independently comprises from about 10 to about 30 g/m2 superabsorbent and from about 40 g m2 to about 65 g/m2 pulp. When it is desired to keep absorbed fluid away from the cover layer 42 the amount of superabsorbent in the first and second middle layers is adjusted such that there is a higher level of superabsorbent in the second middle layer. The superabsorbent in the first and second middle layers can be the same or a different superabsorbent.

In one embodiment, the cellulosic fiber for use in the second absorbent layer 48 is wood pulp. There are certain characteristics of wood pulp that make it particularly suitable for use. Cellulose in most wood pulps has a crystalline form known as Cellulose I which can be converted to a form known as Cellulose II. In the second absorbent layer 48, wood pulp with a substantial portion of the cellulose as Cellulose II could be used. Similarly, pulps having an increased fiber curl value are advantageous. Finally, pulps having reduced levels of hemicellulose are preferred. Means for treating pulps so as to optimize these characteristics are well known in the art. By way of example, treating wood pulp with liquid ammonia is known to convert cellulose to the Cellulose II structure and to increase the fiber curl value. Flash drying is known to increase the fiber curl value of pulp. Cold caustic treatment of pulp decreases hemicellulose content, increases fiber curl and converts cellulose to the Cellulose II form. Thus it could be advantageous that the cellulosic fibers used to produce the material of this invention contain at least a portion of cold caustic treated pulp.

A description of the cold caustic extraction process can be found in U.S. patent application Ser. No. 08/370,571, filed on Jan. 18, 1995, pending which application is a continuation-in-part application of U.S. patent application Ser. No. 08/184,377, now abandoned filed on Jan. 21, 1994. The disclosures of both of these applications are incorporated in their entirety herein by reference.

Briefly, a caustic treatment is typically carried out at a temperature less than about 60 degree C., but preferably at a temperature less than 50 degree C., and more preferably at a temperature between about 10 degree C. to 40 degree C. A preferred alkali metal salt solution is a sodium hydroxide solution newly made up or as a solution by-product in a pulp or paper mill operation, e.g., hemicaustic white liquor, oxidized white liquor and the like. Other alkali metal salts such as ammonium hydroxide and potassium hydroxide and the like can be employed. However, from a cost standpoint, the preferable salt is sodium hydroxide. The concentration of alkali metal salts is typically in a range from about 2 to about 25 weight percent of the solution, and preferably from about 6 to about 18 weight percent. Pulps for high rate, fast absorbing applications are preferably treated with alkali metal salt concentrations from about 10 to about 18 weight percent.

For further details on the structure and the method of construction of the second absorbent layer 48 the reader is invited to refer to the U.S. Pat. No. 5,866,242 granted on Feb. 2, 1999 to Tan et al. The contents of this document are hereby incorporated by reference.

Main Body—Barrier Layer

Underlying the absorbent system 44 is a barrier layer 50 comprising liquid-impervious film material so as to prevent liquid that is entrapped in the absorbent system 44 from egressing the sanitary napkin and staining the wearer's undergarment. The barrier layer 50 is made preferably of polymeric film.

The cover layer 42 and the barrier layer 50 are joined along their marginal portions so as to form an enclosure or flange seal that maintains the absorbent system 44 captive. The joint may be made by means of adhesives, heat-bonding, ultrasonic bonding, radio frequency sealing, mechanical crimping, and the like and combinations thereof. The peripheral seal line is shown in FIG. 1 by the reference numeral 52.

Flaps

The flaps 38 and 40 are preferably made as integral extensions of the cover layer 42 and the barrier layer 50. These integral extensions are joined to one another along their marginal seal portions by adhesives, heat-bonding, ultrasonic bonding, radio frequency sealing, mechanical crimping, and the like and combinations thereof. Most preferably, such joining is made at the same time the cover layer 42 and the barrier layer 50 are bonded to one another to enclose the absorbent system 44. Alternatively, the flaps may include absorbent material between the cover layer and the barrier layer extensions. Such absorbent material may be an extension of the first absorbent layer 46, the second absorbent layer 48 or both.

Adhesive System

Figure 3:
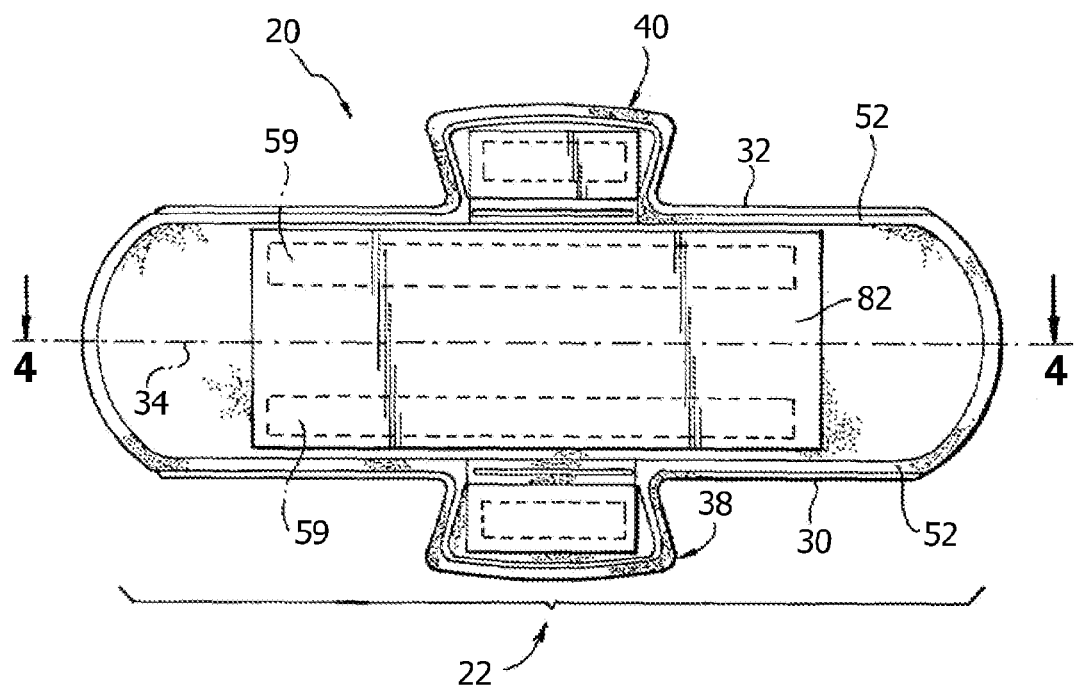
FIG. 3 is a bottom plan view of the sanitary napkin shown in FIG. 1.

Referring to FIGS. 2 and 3, in order to enhance the stability of the sanitary napkin, the garment facing surface of the barrier layer is provided with positioning adhesive material, typically hot-melt adhesive material capable of establishing a temporary bond with the undergarment material. A suitable material is the composition designated HL-1491 XZP commercially available from H. B. Fuller Canada, Toronto, Ontario, Canada. The positioning adhesive is applied to the garment-facing surface of the barrier layer 50 according to a pattern including a pair of linear adhesive zones 59 that extend along the longitudinal axis 34 of the sanitary napkin 20 and are adjacent the side edges of the sanitary napkin 20. The length and the width of the linear adhesive zones 59 may vary according to the intended application. In general, the longer the linear adhesive zones 59 and the wider they are, the higher the bond with the undergarment of the wearer will be. The drawings show the linear adhesive zones 59 as being continuous. This is the preferred form of construction but the continuity of the linear adhesive zones is not an essential element. In a possible variant, the linear adhesive zones may be formed by an array of dots or patches of adhesive arranged to extend along the longitudinal axis 34 of the sanitary napkin and generally adjacent the side edges of the sanitary napkin.

The linear adhesive zones are straight lines that are parallel to one another, but they can also be curved. The straightness of the linear adhesive zones 59 is not an essential character of the invention.

The preferred form of construction of the invention also includes adhesive zones on the flaps 38 and 40.

Standard release paper 82 (shown only in FIG. 3) covers the positioning adhesive pattern before the napkin is used to prevent the unwanted adherence of the napkin to itself or foreign objects. The release paper is of conventional construction (e.g. silicone coated wet-laid Kraft wood pulp) and suitable papers are available from Tekkote Corporation (Leonia, N.J., USA), and bear the designation FRASER 30#/61629.

The main body of the sanitary napkin is provided with a pattern of preferential bending zones to assist the sanitary napkin in folding according to a certain three-dimensional profile in use. In this specification, "three-dimensional deformation profile" means a deformation in the Z direction (vertical direction). FIG. 7 illustrates an example of such three-dimensional profiles. FIG. 7 shows the sanitary napkin 20 of FIG. 1 in cross-section acquiring the "W" pattern where the central portion of the sanitary napkin 20 is raised to form a central upper apex while the zones of the sanitary napkin 20 between the central zone and the longitudinal sides 30, 32 are folded down to form two down apexes. This folding configuration is considered to reduce the likelihood of leakage by virtue of the central upper apex that is positioned close to the vaginal opening of the user, thus it is close to the source of the liquid discharge and as such can better acquire the liquid.

The exemplary sanitary napkin construction depicted in FIG. 1, features a pattern of preferential bending zones having three components, namely pair of preferential bending zones 102 and 104 and a central bending zone 100. The preferential bending zones 102 and 104 are linear (they can follow a straight line or a curved line) and generally extend along the longitudinal axis 34 of the sanitary napkin 20. In the example shown the preferential bending zones 102 and 104 are slightly arcuate, and more particularly they curve inwardly with relation to the side edges of the sanitary napkin 20. The preferential bending zones 102 and 104 can also be straight. The preferential bending zones 102 and 104 are adjacent the side edges of the sanitary napkin 20 and preferably extend along a major portion of the sanitary napkin length. In a specific example of implementation, the preferential bending zones 102 and 104 have a length that is at least 50% of the total length of the sanitary napkin 20 and preferably more.

The preferential bending zones 102 and 104 register with respective longitudinal adhesive zones 59. In this specification, "registering" means that a preferential bending zone has in general terms the same longitudinally extending orientation as the associated longitudinal adhesive zone 59 and that at least a portion of the preferential bending zone is substantially vertically aligned with the longitudinal adhesive zone 59. "Registering" does not necessarily imply that a preferential bending zone and that the associated longitudinal adhesive zone 59 are of the same extent or the same precise geometrical form (straight line or curved line) or precisely aligned with one another. Preferably, a condition of alignment exists, such that the preferential bending zone is contained within the boundaries of the associated longitudinal adhesive zone.

The sanitary napkin also includes a central preferential bending zone 100 that is formed at the crossing points of a plurality of oblique preferential bending lines intersecting each other. The oblique preferential bending lines are arcuate and are created on the cover layer and absorbent system. Under this specific example of implementation, the preferential bending lines cross one another and form an array of crossing points. The crossing points are located on the longitudinal axis of the sanitary napkin and structurally weaken the sanitary napkin at that location allowing the sanitary napkin to fold preferentially at its longitudinal axis when subjected to lateral compression. It is the array of crossing points that forms the central preferential bending zone 100.

Each preferential bending line of the array of bending lines whose crossing points forms the central preferential bending zone 100 extends generally along an angle of 45 degrees with respect to the longitudinal axis 34 of the main body of the sanitary napkin 20. The pattern is designed such that each preferential bending line intersects at least two other preferential bending lines. Also, each preferential bending line extends from one longitudinal side area of the sanitary napkin to the opposite longitudinal side area, crossing the imaginary longitudinal axis of the sanitary napkin. A longitudinal side area is defined as a portion of the sanitary napkin that extends inwardly from a respective longitudinal side edge 30, 32, the side edge forming the outer boundary of the side area (the longitudinal side edge is considered part of the longitudinal side area). Each side area has a width that is about 25% of the maximal transverse dimension of the main body 22 (excluding the flaps).

Without intent of being bound by a specific theory, it is believed that the plurality of oblique preferential bending lines contribute to increase the flexural resistance of the sanitary napkin which has the effect of stabilising the sanitary napkin against bunching. At the same time, the oblique preferential bending lines form the central preferential bending zone 100 at their crossing points.

In a specific example, the spacing between preferential bending lines is about 2 cm.

In an alternative embodiment, the preferential bending zones 100, 102 and 104 are created on the absorbent system only, such as on the first absorbent layer 42, the second absorbent layer 48 or both, so that the preferential bending zones 100, 102 and 104 are less visible on the sanitary napkin than when the preferential bending zones 100, 102 and 104 are made on the cover layer and absorbent system.

In another alternative embodiment, a single longitudinally extending continuous bending line extending along the longitudinal axis 34 of the sanitary napkin 20 can replace the array crossing points.

As discussed earlier, the pattern of bending zones on the sanitary napkin 20 can assist the sanitary napkin to acquire a three-dimensional deformation profile. The three-dimensional deformation profile includes a "W" profile, among other possible profiles. The embodiment of the invention shown in FIG. 1 is designed to preferentially fold according to the "W" pattern, as shown in FIG. 7. When the sanitary napkin 20 is subjected to lateral compression, it folds up at the longitudinal axis 34 forming a central apex 200 at that location and also folds down at the two longitudinally extending preferential bending zones 102 and 104 forming two down apexes 202 and 204. The condition of registration between the preferential zones 100 and 102 and the longitudinal adhesive zones 59 facilitates the formation of the two down apexes 202 and 204 by bonding the sanitary napkin to the undergarment of the wearer at the area where the fold is to occur in response to lateral compression. This allows the sanitary napkin 20 to behave in a more predictable manner by folding where it is desired rather than in a random and uncontrolled manner.

Method of Manufacture

The above-described embodiment of the sanitary napkin 20 is fabricated in a conventional manner in accordance with conventional techniques. Specifically, a laminate structure, sometimes referred to in the art as a web, is created. This laminate structure comprises an expanse of the materials from which the napkin will be created. I.e. the laminate structure comprises the following layers of material in a top-to-bottom order: an expanse of cover layer material; an expanse of first absorbent layer material; an expanse of second absorbent layer material (manufactured as described above); and finally an expanse of barrier layer material. Some of the materials are necessarily not continuous within the laminate structure, and where such is the case, they are positioned precisely, one with respect to another, in the relationship they will occupy in the final products. The cover layer material and the barrier layer material are then bonded together by applying pressure in the appropriate positions, and what will become the peripheral seal is created. The seal may also be made by means of heat-bonding, ultrasonic bonding, radio frequency sealing, mechanical crimping, and the like and combinations thereof. The sealed structure is then severed by conventional means (i.e. die-cutting, fluid-jet cutting, or by laser) from the web to create a discrete article.

The central preferential bending zone 100 and the preferential bending zones 102 and 104 are created preferably by embossing. The choice of embossing is not critical since the same result may be obtained by other methods also such as slitting, perforating or other techniques known to those skilled in the art. If the embossing operation is chosen to create the preferential bending zones, the sanitary napkin is passed between a pair of rolls, one of the rolls including projections according to the pattern of embossing desired. The projections locally compress the material of the sanitary napkin, which can be a either combination of the cover layer and the absorbent system or the absorbent system alone, thereby compacting it. The degree of pressure applied during the embossing operation can vary depending upon the type of material embossed and the physical integrity of the material embossed, among others. It is within the reach of a person skilled in the art to find the optimal process conditions in accordance with the specific application. In general, the embossing pressure should be selected to sufficiently densify the material locally so as to create the preferential bending zones and at the same time not to be too high so as to sever the material. Heating the embossing rolls has been found beneficial. Also, ultrasonic embossing may be used for forming the preferential bending zones.

It is preferred to emboss the entire sanitary napkin as the embossing also holds the various layers of the sanitary napkin together and reduces the likelihood of the cover layer or the barrier layer gapping or coming loose when the sanitary napkin is bent.

The positioning adhesive material is then applied to the barrier layer to create the longitudinal adhesive zones 59, and any other adhesive zones as the case may be, and release paper is applied to cover the positioning adhesive. Alternatively, the positioning adhesive, or the positioning adhesive and the release paper may be applied to the web before the individual articles are severed therefrom.

As indicated earlier, the sanitary napkin 20 has a thickness of about 5 mm or less. The apparatus required to measure the thickness of the sanitary napkin is a footed dial (thickness) gauge, available from Ames, with foot 1⅛" diameter with stand, 2 oz. deadweight accurate to 0.001". A digital type apparatus is preferred. If the sanitary napkin sample is individually folded and wrapped, the sample is unwrapped and carefully flattened by hand. The release paper is removed from the sample and it is repositioned back gently across the positioning adhesive lines so as not to compress the sample, ensuring that the release paper lies flat across the sample. Flaps (if any) are folded back under the sample, prior to taking the thickness reading in the center of the sample.

The foot of the gauge is raised and the sample is placed on the anvil such that the foot of the gauge is approximately centered to the sample (or in the location of interest on the sample of interest). When lowering the foot, care is taken to avoid allowing the foot to "drop" or that undue force is not applied. The read out is allowed to stabilize for approximately 5 seconds. The thickness reading is then taken.

The flexural resistance of the sanitary napkin is preferably in the range from about 400 g to about 800 g. The flexural resistance of a sanitary napkin is measured by peak bending stiffness. Peak bending stiffness is determined by a test that is modeled after the ASTM D 4032-82 CIRCULAR BEND PROCEDURE, the procedure being considerably modified and performed as follows. The CIRCULAR BEND PROCEDURE is a simultaneous multi-directional deformation of a material in which one face of a specimen becomes concave and the other face becomes convex. The CIRCULAR BEND PROCEDURE gives a force value related to flexural resistance, simultaneously averaging stiffness in all directions.

The apparatus necessary for the CIRCULAR BEND PROCEDURE is a modified Circular Bend Stiffness Tester, having the following parts:

1. A smooth-polished steel plate platform which is 102.0 mm by 102.0 by 6.35 mm having an 18.75 mm diameter orifice. The lap edge of the orifice should be at a 45 degree angle to a depth of 4.75 mm;
2. A plunger having an overall length of 72.2 mm, a diameter of 6.25 mm, a ball nose having a radius of 2.97 mm and a needle-point extending 0.88 mm therefrom having a 0.33 mm base diameter and a point having a radius of less than 0.5 mm, the plunger being mounted concentric with the orifice and having equal clearance on all sides. Note that the needle-point is merely to prevent lateral movement of the test specimen during testing. Therefore, if the needle-point significantly adversely affects the test specimen (for example, punctures an inflatable structure), than the needle-point should not be used. The bottom of the plunger should be set well above the top of the orifice plate. From this position, the downward stroke of the ball nose is to the exact bottom of the plate orifice;
3. A force-measurement gauge and more specifically an Instron inverted compression load cell. The load cell has a load range of from about 0.0 to about 2000.0 g;
4. An actuator and more specifically the Instron Model No. 1122 having an inverted compression load cell. The Instron 1122 is made by the Instron Engineering Corporation, Canton, Mass.

In order to perform the procedure for this test, as explained below, five representative sanitary napkins are necessary. From one of the five napkins to be tested, some number "Y" of 37.5 mm by 37.5 mm test specimens are cut. Specimens having portions in which a cover layer is joined directly to a barrier layer or which are a laminate of a cover layer, and a barrier layer without any component of the absorbent system, should not be tested. This test is more concerned with the overall flexibility of the sanitary napkin and not merely the peripheral portions thereof and, therefore, the flexibility of the present invention is more concerned with the flexibility of the absorbent portions of the sanitary napkin.

The test specimens should not be folded or bent by the test person, and the handling of specimens must be kept to a minimum and to the edges to avoid affecting flexural-resistance properties. From the four remaining sanitary napkins, an equal number "Y" of 37.5 mm by 37.5 mm specimens, identical to the specimens cut from the first napkin, are cut. Thus, the test person should have "Y" number of sets of five identical specimens.

The procedure for the CIRCULAR BEND PROCEDURE is as follows. The specimens are conditioned by leaving them in a room that is 21 degree Celsius plus or minus 0.1 degree Celsius. and 50% plus or minus 2.0% relative humidity for a period of two hours. The test plate is leveled. The plunger speed is set at 50.0 cm per minute per full stroke length. A specimen is centered on the orifice platform below the plunger such that the cover layer 42 of the specimen is facing the plunger and the barrier layer 50 of the specimen is facing the platform. The indicator zero is checked and adjusted, if necessary. The plunger is actuated. Touching the specimen during the testing should be avoided. The maximum force reading to the nearest gram is recorded. The above steps are repeated until all five of the identical specimens have been tested.

CALCULATIONS

The peak bending stiffness for each specimen is the maximum force reading for that specimen. Remember that "Y" number of sets of five identical specimens were cut. Each set of five identical specimens is tested and the five values received for that set are averaged. Thus, the test person now has an average value for each of the 'Y' sets tested. The flexural resistance for a sanitary napkin is the greatest of these average peak bending stiffnesses.

Applications of the product and methods of the present invention for sanitary and other health-care uses can be accomplished by any sanitary protection, incontinence, medical and absorbent methods and techniques as are presently or prospectively known to those skilled in the art. Thus, it is intended that the present application cover the modifications and variations of this invention provided that they come within the scope of the appended claims and their equivalents.

We claim:

1. A sanitary napkin adapted to be worn in a crotch portion of an undergarment said sanitary napkin comprising a main body with a longitudinal axis and two opposite longitudinal side areas, said main body further comprising:
    a) a fluid-pervious cover layer;
    b) an absorbent system under said cover layer;
    c) a liquid-impervious barrier layer under said absorbent system;
    d) said sanitary napkin being characterised by a thickness less than about 5 mm;
    said liquid-impervious barrier layer including a pair of linear adhesive zones that extend along said longitudinal axis and are adjacent to respective side edges of the sanitary napkin, said linear adhesive zones being capable of bonding said sanitary napkin to the undergarment;
    said main body including a preferential bending line extending obliquely in relation to said longitudinal axis on said main body, said preferential bending line extending from one longitudinal side area of the sanitary napkin to an opposite longitudinal side area, crossing the longitudinal axis of the sanitary napkin; and
    wherein said sanitary napkin is characterized by a flexural resistance of not less than about 400 g.

2. A sanitary napkin as defined in claim 1, wherein said sanitary napkin has two opposite longitudinal side areas, said sanitary napkin including a preferential bending line extending obliquely in relation to said longitudinal axis, said preferential bending line extending from one longitudinal side area of the sanitary napkin to an opposite longitudinal side area, crossing the longitudinal axis of the sanitary napkin.

3. A sanitary napkin as defined in claim 2, wherein said sanitary napkin includes a plurality of preferential bending lines crossing one another and defining an array of crossing points.

4. A sanitary napkin as defined in claim 3, wherein the crossing points in the array of crossing points extend along said longitudinal axis and facilitate folding of said sanitary napkin at a location along the longitudinal axis, said array of crossing points forming a central preferential bending zone.

5. A sanitary napkin as defined in claim 1, wherein said main body is capable of acquiring a three dimensional deformation profile in the form of a W profile.

6. A sanitary napkin as defined in claim 1, wherein said preferential bending zones are formed by a process selected from the group consisting of perforating, slitting, cutting and embossing.

7. A sanitary napkin as defined in either claim 1, wherein said preferential bending zones are arcuate.

8. A sanitary napkin as defined in claim 7, wherein said absorbent system includes superabsorbent material.

9. A sanitary napkin as defined in claim 8, wherein said absorbent system includes a blend of cellulosic fibers and superabsorbent material.

10. A sanitary napkin as defined in claim 9, wherein said absorbent system includes an absorbent layer having a basis weight of from about 100 g/m2 to about 700 g/m2 which has been air-laid as a bottom stratum of pulp, a middle stratum of pulp and superabsorbent polymer disposed in amongst the pulp, and a top stratum containing at least some pulp.

11. A sanitary napkin as defined in claim 10, wherein said absorbent system includes a plurality of absorbent layers in a superposed condition.

12. A sanitary napkin as defined in claim 1, wherein said preferential bending zones are aligned with respective longitudinal adhesive zones.

13. A sanitary napkin as defined in claim 1, wherein said sanitary napkin includes a flap projecting from a side edge of said sanitary napkin, said flap being foldable about an edge of the crotch portion for retaining said sanitary napkin on the undergarment.

* * * * *